US008958999B1

(12) United States Patent  
Ptasinski et al.

(10) Patent No.: US 8,958,999 B1  
(45) Date of Patent: Feb. 17, 2015

(54) DIFFERENTIAL DETECTION FOR SURFACE PLASMON RESONANCE SENSOR AND METHOD

(75) Inventors: Joanna N. Ptasinski, La Jolla, CA (US); Lin Pang, San Diego, CA (US); Pang-Chen Sun, San Diego, CA (US); Boris Slutsky, San Diego, CA (US); Yeshaiahu Fainman, San Diego, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 870 days.

(21) Appl. No.: 13/195,057

(22) Filed: Aug. 1, 2011

(51) Int. Cl.
 *G01R 13/00* (2006.01)
(52) U.S. Cl.
 USPC .............................................. 702/66
(58) Field of Classification Search
 USPC .............................................. 702/66
 See application file for complete search history.

(56) References Cited

U.S. PATENT DOCUMENTS

2002/0056816 A1\* 5/2002 Stark ........................... 250/493.1
2009/0046275 A1\* 2/2009 Jefferson et al. .............. 356/73

OTHER PUBLICATIONS

C. Lausted, Z. Hu, Leroy Hood, "Quantitative Serum Proteomics from Surface Plasmon Resonance Imaging," Molecular & Cellular Proteomics 7.12, 2464-2474 (2008).

C. Shaffer, "Naked Proteomics," Genomics and Proteomics 7, G6-G7, (2007).
J. Homola, "Surface Plasmon Resonance Sensors for Detection of Chemical and Biological Species," Chem. Rev.,108, 462-493 (2008).
N. Blow, Nature Methods 6, 389-393 (2009).
R. Slavik and J. Homola, "Ultrahigh resolution long range surface plasmon-based sensor," Sensors and Actuators B 123, 10-12 (2007).
X.Y. Yang, D.M. Liu, W.C. Xie, and C.F. Li "High sensitivity sensor based on surface plasmon resonance enhanced lateral optical beam displacements," Chin. Phys. Lett. 24, 458-461 (2007).
A. Naimushin, S.D. Soelberg, D.U. Bartholomew, J.L. Elkind, and C.E. Furlong, "Portable surface plasmon resonance (SPR) Sensor system with temperature stabilization," Sensors and Actuators B: Chemical 96, 253-260 (2003).
K. Tetz, L. Pang, and Y. Fainman, "High-resolution surface plasmon resonance sensor based on linewidth-optimized nanohole array transmittance," Opt. Lett. 31, 1528-1530 (2006).
L. Pang, G. Hwang, B.Slutsky and Y. Fainman, "Spectral sensitivity of two-dimensional nanohole array surface plasmon polariton resonance sensor," Appl. Phys. Lett. 91, 123112 (2007).
Y. Fainman, E. Lenz, and J. Shamir, "Optical profilometer: a new method for high sensitivity and wide dynamic range," Applied Optics 21, 3200-3208 (1982).

(Continued)

*Primary Examiner* — Aditya Bhat
(74) *Attorney, Agent, or Firm* — SPAWAR Systems Center Pacific; Kyle Eppele; Stephen E. Baldwin

(57) ABSTRACT

A differential measurement design employing two nearly collinear optical beams provides surface plasmon polariton resonance (SPR) sensors and a corresponding method of increased dynamic range and signal to noise ratio. The differential measurement device and method based on wavelength interrogation, employs a single incident polarization state, and is combined with a 2-D nanohole array for operation at near-normal incidence, where this approach offers a decrease in the measurement time.

16 Claims, 11 Drawing Sheets

(56) References Cited

OTHER PUBLICATIONS

W. Zhao, R. Sun, L. Qiu, and D. Sha, "Laser differential confocal ultra-long focal length measurement," Optics Express 17, 20051-20062 (2009).

T.R. Corle, J.T. Fanton, and G.S. Kino, "Distance measurements by differential confocal optical ranging," Applied Optics 26, 2416-2420 (1987).

L. Pang, W. Nakagawa, and Y. Fainman, "Fabrication of 2-D photonic crystals with controlled defects by use of multiple exposures and direct-write," Applied Optics 42, 5450-5456 (2003).

A. Groisman, S. Zamek, K. Campbell, L. Pang, U. Levy, and Y. Fainman, "Optofluidic 1×4 switch," Optics Express 16, 13499-13508 (2008).

I. Thormählen, J. Straub, and U. Grigull, "Refractive index of water and its dependence on wavelength, temperature, and density," J. Phys. Chem. Ref. Data 14, 933-945 (1985).

\* cited by examiner

1) Muliplexing duplex channels (overlapped on each other's waist)

2) Difference in the DTFs of the two channels
(3) Zero-crossing detection

DIFFERENTIAL DETECTION FOR SURFACE PLASMON RESONANCE SENSOR AND METHOD

FEDERALLY-SPONSORED RESEARCH AND DEVELOPMENT

This invention (Navy Case NC 100,978) is assigned to the United States Government and is available for licensing for commercial purposes. Licensing and technical inquiries may be directed to the Office of Research and Technical Applications, Space and Naval Warfare Systems Center, Pacific, Code 72120, San Diego, Calif., 92152; voice (619) 553-5118; email ssc_pac_t2@navy.mil

BACKGROUND OF THE INVENTION

The development of disease-related biomarker panels requires fast and efficient methods for obtaining multi-parameter protein profiles. Commonly used fluorescent labeling processes are easy to implement, but they disrupt the accurate measurement of kinetic constants and can lead to antibody cross-reactivity problems. An alternative, label-free biodetection method utilizes the phenomenon of surface plasmon polariton (SPP) resonance. SPP based devices integrate microfluidic channels with metal-dielectric layer chips, and measure transmittance or reflectance of light, hereafter referred to as Device Transfer Function (DTF), at the metal-fluid interface. The DTF exhibits a sharp resonant feature when the probe wavelength and the angle of incidence satisfy the condition for SPP excitation.

SUMMARY OF THE INVENTION

In one preferred embodiment, the present invention is related to a method in a surface plasmon resonance sensor having a metal-dielectric interface formed by microfluidic channels integrated with metal-dielectric layer chips. In that preferred embodiment, the method comprises the steps of imaging a pair of collimated laser beams at different angles of incidence onto substantially the same spot on a metal nanohole array sample at the metal-dielectric interface to excite surface plasmons on the array sample and forming a pair of transmitted laser beams emerging from the array sample; forming a pair of parallel laser beams corresponding to the pair of transmitted laser beams; obtaining a pair of device transfer function (DTF) signals from the pair of parallel laser beams, where each respective DTF signal has a different angle of incidence and an intensity peak at a different wavelength relative to a reference wavelength; and calculating a difference signal from the pair of DTF signals, where the difference signal has positive and negative values about a zero crossing axis which are representative of transmittivity relative to wavelength and where a resulting shift in the location of the difference signal at the zero crossing axis represents a changing refractive index of the dielectric at the metal-dielectric interface.

BRIEF DESCRIPTION OF THE DRAWINGS

The invention will be more fully described in connection with the accompanying drawings, where like reference numerals designate like components, in which.

DETAILED DESCRIPTION OF THE PREFERRED EMBODIMENTS

As has been described above, the development of disease-related biomarker panels will require fast and efficient methods for obtaining multiparameter protein profiles. Commonly used fluorescent labeling processes are easy to implement, but they disrupt the accurate measurement of kinetic constants and can lead to antibody cross-reactivity problems. An alternative, label-free biodetection method utilizes the phenomenon of surface plasmon polariton (SPP) resonance. SPP based devices integrate microfluidic channels with metal-dielectric layer chips, and measure transmittance or reflectance of light, hereafter referred to as Device Transfer Function (DTF), at the metal-fluid interface. The DTF exhibits a sharp resonant feature when the probe wavelength and the angle of incidence satisfy the condition for SPP excitation. The location of the resonance depends on the refractive index of the fluid, and therefore informs on its biochemical composition.

Figure 1:
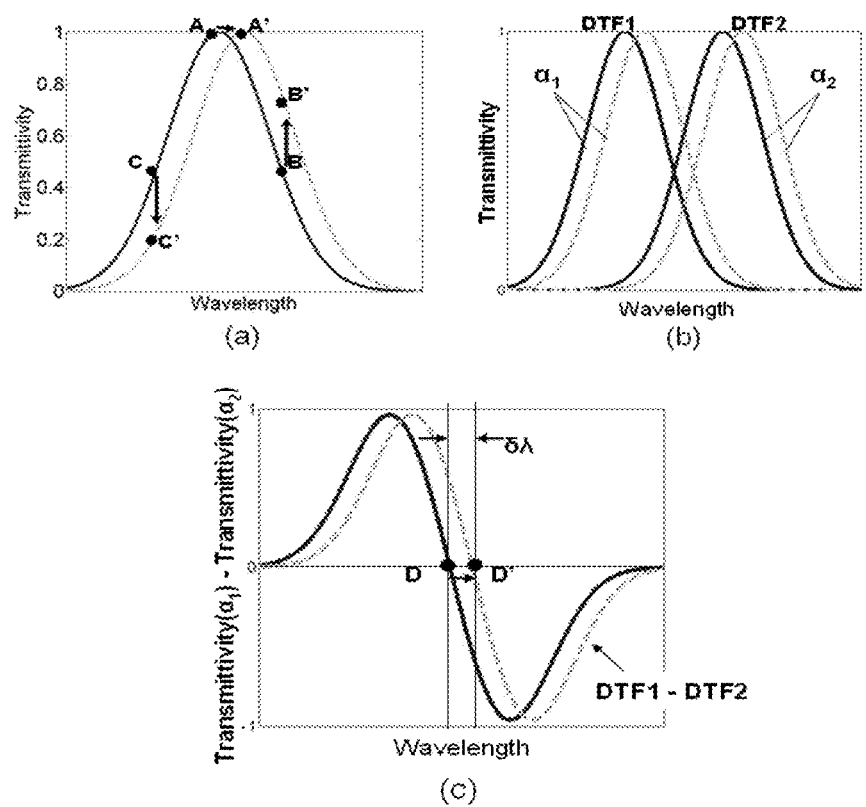
FIG. 1a shows a typical SPR scheme to determine the location of resonance.
FIG. 1b shows how DTFs are constructed at different angles of incidence.
FIG. 1c shows the differential of two DTFs constructed at different angles of incidence.

FIG. 1a shows typical SPR (Surface Plasmon Resonance) schemes which determine the location of the resonance by monitoring a shift in point A to A' or monitoring the shift in intensity at a single wavelength/angle value B to B' or C to C'.

FIG. 1b shows differential detection in which two DTFs (DTF1, DTF2) are constructed at different angles of incidence α1, α2. As shown in FIG. 1b, when the refractive index changes, both DTFs shift in the same direction.

FIG. 1c shows the differential (DTF1−DTF2) of the two DTFs constructed at different angles of incidence and the resulting shift in the differential as a function of changing refractive index. The differential signal DTF1−DTF2 in FIG. 1c shows the shifting δλ between points D-D' at the zero crossing axis, where the difference signal is shown as change of transmittivity (y-axis) relative to wavelength (x-axis).

The SPP based techniques are broadly classified into wavelength interrogation, angular interrogation, and intensity interrogation families. In wavelength (angular) interrogation, multiple measurements of the DTF are made at different wavelengths (respectively, angles of incidence), such that the location of the resonance may be identified by a curve fit (FIG. 1a, shift in point A to A'). The intensity interrogation method relies on a single measurement at a fixed angle and wavelength (FIG. 1a, shift in points B to B' or C to C'). Intensity interrogation devices are thus simpler than wavelength and angular interrogation devices, but typically less accurate. This is because changes of the magnitude and width of the DTF cannot be distinguished from a change in its location.

Here we describe a differential intensity interrogation method, where two measurements of the DTF are made simultaneously at nearly equal incident angles, and their difference is constructed (FIG. 1b and FIG. 1c). The zero-crossing of the difference signal can be tracked with a tunable light source in a closed-loop system, similarly to the way in which beam position is tracked using quadrant detectors, resulting in a robust measurement.

Closed-loop tracking of the zero crossing is performed continuously and does not require an end-to-end wavelength sweep for each measurement. Our device also utilizes a metal film perforated with a 2-D array of nanoholes, as in Tetz et al. With this technique, SPP resonance can be achieved at normal or near-normal incidence, permitting measurement over a large area not limited by the focal depth of the imaging optics.

Described initially is a short review of the theory and concepts associated with plasmonic detection and differential measurement. Fabrication methods used for the nanohole arrays and the fluidic chambers are then discussed in full detail. Lastly, our optical setup, the measurement method and the measurement results for our differential detection scheme are presented.

In our plasmonic nanosensor design, the shape of a DTF curve most closely resembles that of a singly peaked normalized Lorentzian function, which can be described by:

$$T_L(\lambda) = \frac{1}{1+\left(\frac{\lambda-\lambda_0}{\frac{1}{2}w}\right)^2} \quad (1)$$

where $\lambda$ is the wavelength, $\lambda_0$ points to the location where the maximum of the DTF occurs, and w is the parameter specifying the Full Width at Half Maximum (FWHM). The centerpoint $\lambda_0$ and the FWHM w of each DTF excited through a nanohole array depend on the permittivity of the metal, the refractive index of the dielectric material, the period of the grating array, and the angle of incidence.

The width of the SPR DTF curve (the FWHM of the Lorentzian) is directly related to the fill factor of the nanohole array, since a large size hole diameter increases surface wave scattering and broadens the resonance linewidth.

Our Rigorous Coupled Wave Analysis (RCWA) simulation results for a 1D gold nanohole array show a 72% decrease in the FWHM of DTF when the gold fill factor is increased from 0.5Λ to 0.9Λ. It should be noted that while small diameter holes give rise to a narrow FWHM, they are more difficult to fabricate and they also don't allow for as much light to pass through the array in the transmission regime ensuing in a lower intensity signal. In one embodiment, our method of utilizing a polarizer/analyzer pair enables us to pick up any DTF signal that may be present and suppress all other light transmission.

For our experiment we chose the gold fill factor to be 60% as a trade-off between signal transmission and sharpness of the DTF. However, other fill factors can also be used, depending on the desired gain and linear range of the feedback signal and the noise floor of the detection system.

For example, an 85% fill yields (according to our RCWA simulations) 3 times narrower DTFs in FIG. 1(b) than a 60% fill, and hence 3 times steeper differential slope in FIG. 1(c), but it would also reduce transmitted intensity by a factor of 2.5.

Figure 3:
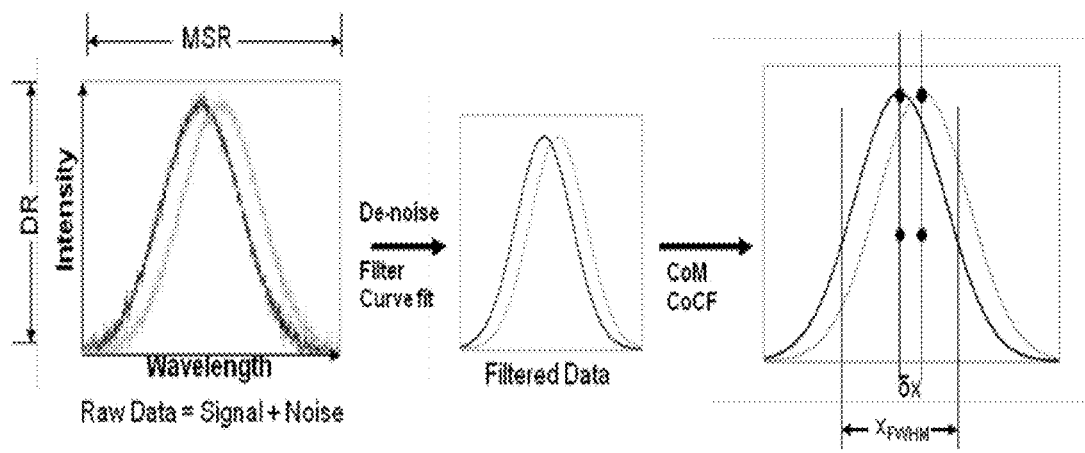
FIG. 3 shows illustrations of challenges for DTF detection.

Challenges for Device Transfer Function (DTF) Detection are shown in FIG. 3. Location of the Device Transfer Function (DTF) allows for the monitoring of surface chemistry Traditional DTF detection schemes include:
Signal peak detection=>low accuracy due to noisy background
First moment or CoM detection=>high accuracy but time consuming
Curve fitting=>accurate but even more time consuming
where the acronyms in FIG. 3 are:
DTF—Device Transfer Function
CoM—Center of Mass
CoCF—Center of Curve Fit
MSR—Measured Spectral Range
DR—Dynamic Range FIG. 4a shows a conceptual block diagram of the present invention, FIG. 4b shows multiplexing duplex channels (overlapped on each other's waist and FIG. 4c shows the difference in the DTFs of the two channels and the zero crossing detection.

As noted, wavelength and angular interrogation methods require multiple measurements of the DTF, which increases measurement time. Our approach involves just two measurements, one for each of the two DTFs $T_1$, $T_2$, corresponding to distinct angles of incidence, and the construction of their difference $T_1-T_2$. Unlike the individual DTFs, the difference signal crosses zero (FIG. 1c) and this location of zero crossing depends only on the locations of the DTFs and not on their magnitude and width. Instead of measuring at the point of maximum signal strength from a DTF curve (i.e., A→A' in FIG. 1a), measure the points that are most sensitive with respect to change of the DTF (i.e., C→C' and B→B' in FIG. 1a). The difference signal has a greater linear range than the individual DTFs, as seen in FIG. 1c and FIG. 4c. Both these features are advantageous in a measurement system that tracks the zero crossing with a closed-loop controller, as shown in FIG. 4a.

Figure 4A:
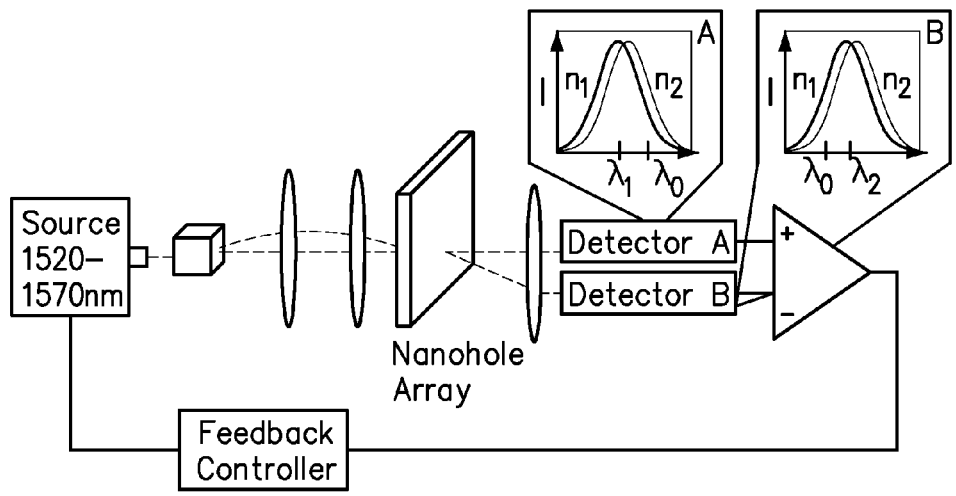
FIG. 4a shows a concept block diagram for differential detection.
Figure 4B:
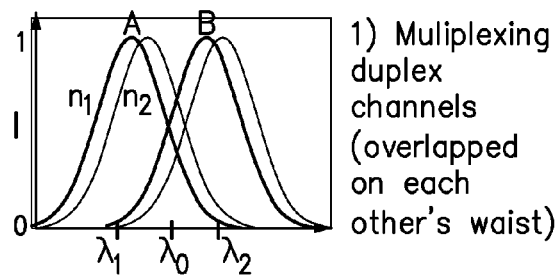
FIG. 4b shows multiplexing duplex channels.
Figure 4C:
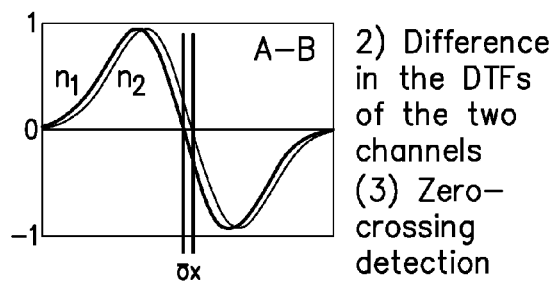
FIG. 4c shows the difference in the DTFs of the two channels.

The closed-loop configuration shown in FIG. 4a includes a laser means for imaging a pair of laser beams onto a nanohole array to excite surface plasmon resonance and form a pair of transmitted laser beam emerging from the nanohole array. The laser means then forms a pair of transmitted parallel laser beams emerging from the nanohole array which impinge on a pair of detectors (detector A and detector B). A processor means obtains a pair of device transfer function (DTF) signals from the pair of parallel laser beams, where each respective DTF signal has a different angle of incidence and an intensity peak at a different wavelength relative to a reference wavelength. The processor means calculates a difference signal from the pair of DTF signals, where the difference signal has positive and negative values about a zero crossing axis which are representative of transmittivity relative to wavelength and where a resulting shift in the location of the difference signal at the zero crossing axis represents a changing refractive index of the dielectric at the metal-dielectric interface.

As will become apparent, advantages of the present invention are:
Only two data points required
Immune to the power fluctuation of source since it impacts both DTFs equally
Reduction of some systematic errors
Suitable for feedback loop devices When the two Lorentzians $T_1$, $T_2$ are centered respectively at wavelengths $\lambda_1$, $\lambda_2$, the slope $\partial(T_1-T_2)/\partial\lambda$, which is a measure of the linear region of the difference between two DTFs, is expressed as $$T'_D(\lambda)|_{\lambda_1-\lambda_2} = \frac{\partial}{\partial\lambda}\left[\left(1+\left(\frac{\lambda-\lambda_1}{\frac{1}{2}w}\right)^2\right)^{-1} - \left(1+\left(\frac{\lambda-\lambda_2}{\frac{1}{2}w}\right)^2\right)^{-1}\right] \quad (2)$$

This slope is plotted in FIG. 2 for various separations between the center of $T_1$ and $T_2$. In a closed-loop control system, a steep slope improves measurement sensitivity, while a wider linear region is desirable to make the controller more robust. FIG. 2 illustrates the tradeoff between these two parameters. In the present work, we chose $\lambda_1-\lambda_2$=FWHM as a reasonable compromise.

Differential detectors have long been utilized in confocal microscopy, range finding, etc. An advantage of differential measurement is the unique property of self-referencing for optical source fluctuation, since any fluctuation of the intensity will impact the adjacent DTFs equally and thus cancel itself. This concept has been widely adapted by the telecommunication industry, where differential signals are used to carry the bits that eliminate the cause of "ground" noise.

Figure 2A:
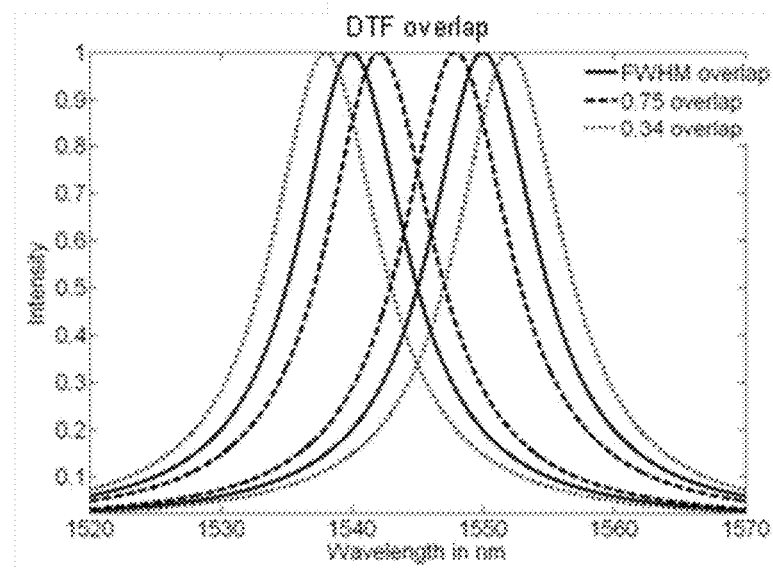
FIG. 2a shows DTF overlap.

FIG. 2a shows the DTF overlap of intensity relative to wavelength and

Figure 2B:
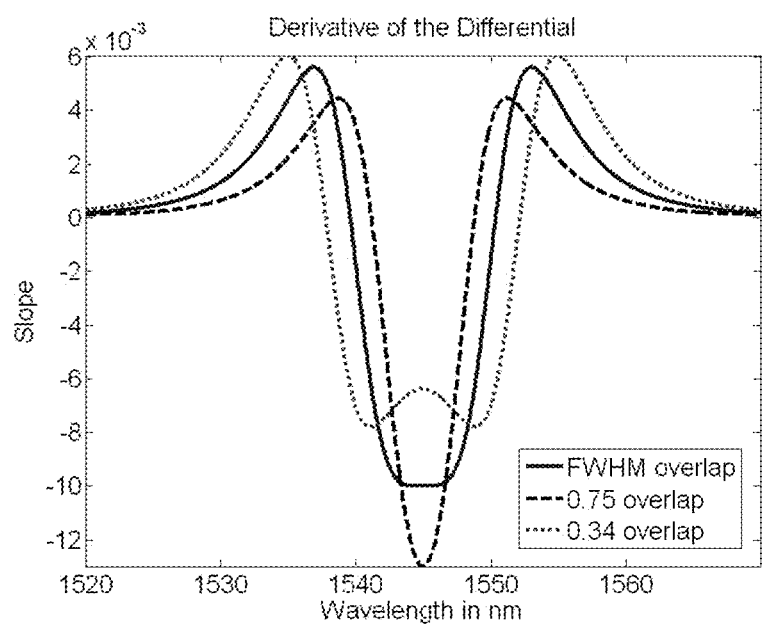
FIG. 2b shows the derivative of the DTF differential.

FIG. 2b shows the derivative of the DTF differential, $T_D$=T $(\lambda_1)$−T$(\lambda_2)$, when the DTF curves are overlapped at the 0.5 transmittivity value (solid curve), 0.75 value (dashed curve), and the 0.34 point (dotted curve).

Figure 5A:
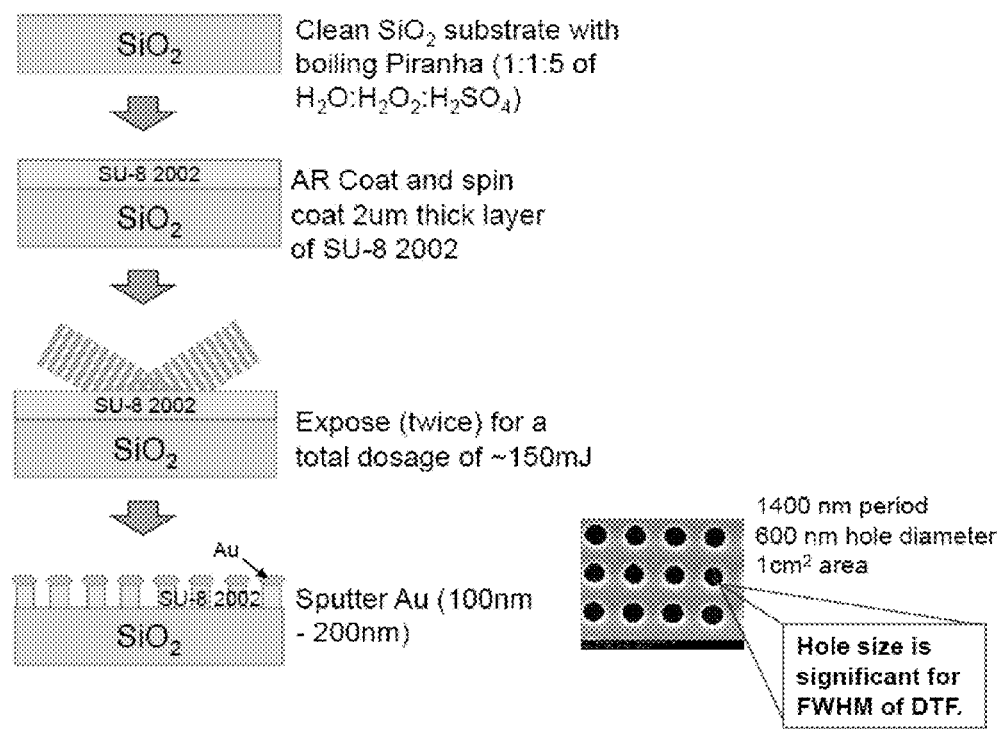
FIG. 5a and FIG. 5b show the fabrication steps for fabricating the gated array samples utilized with the present invention.
Figure 5B:
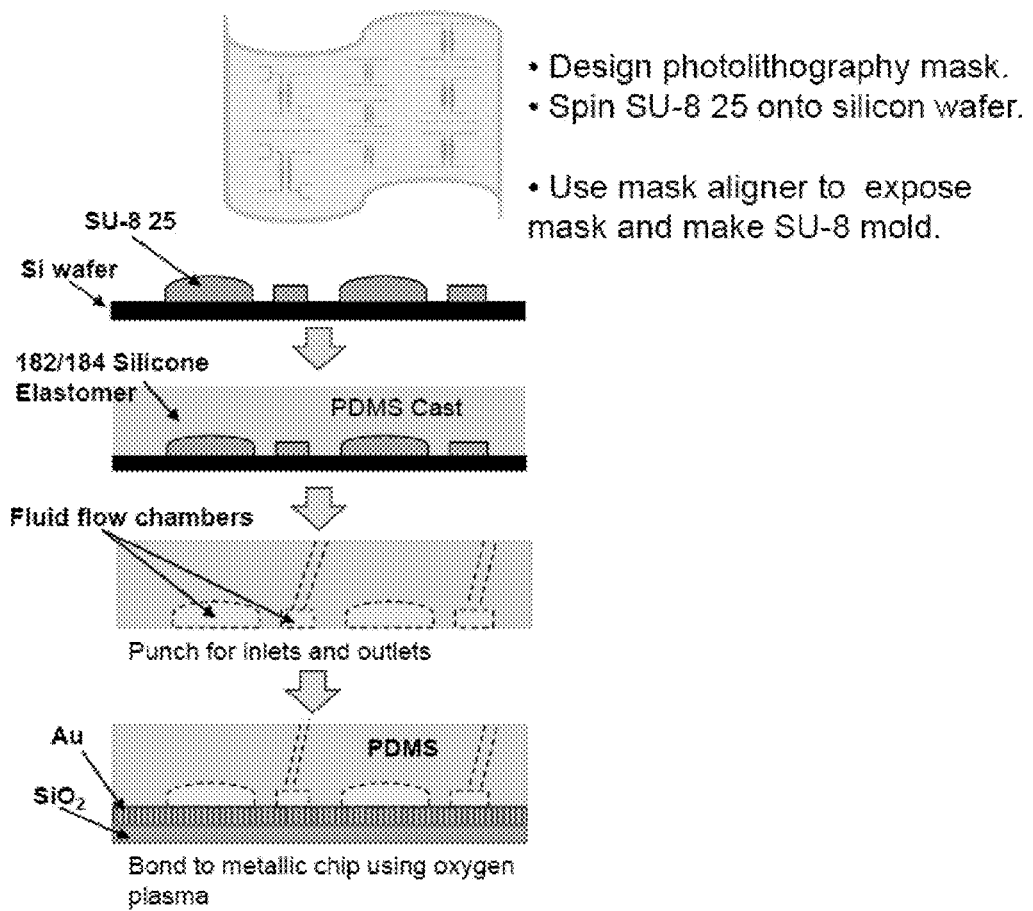

As shown in FIGS. 5a and 5b, the samples (one of which is also shown in

Figure 6:
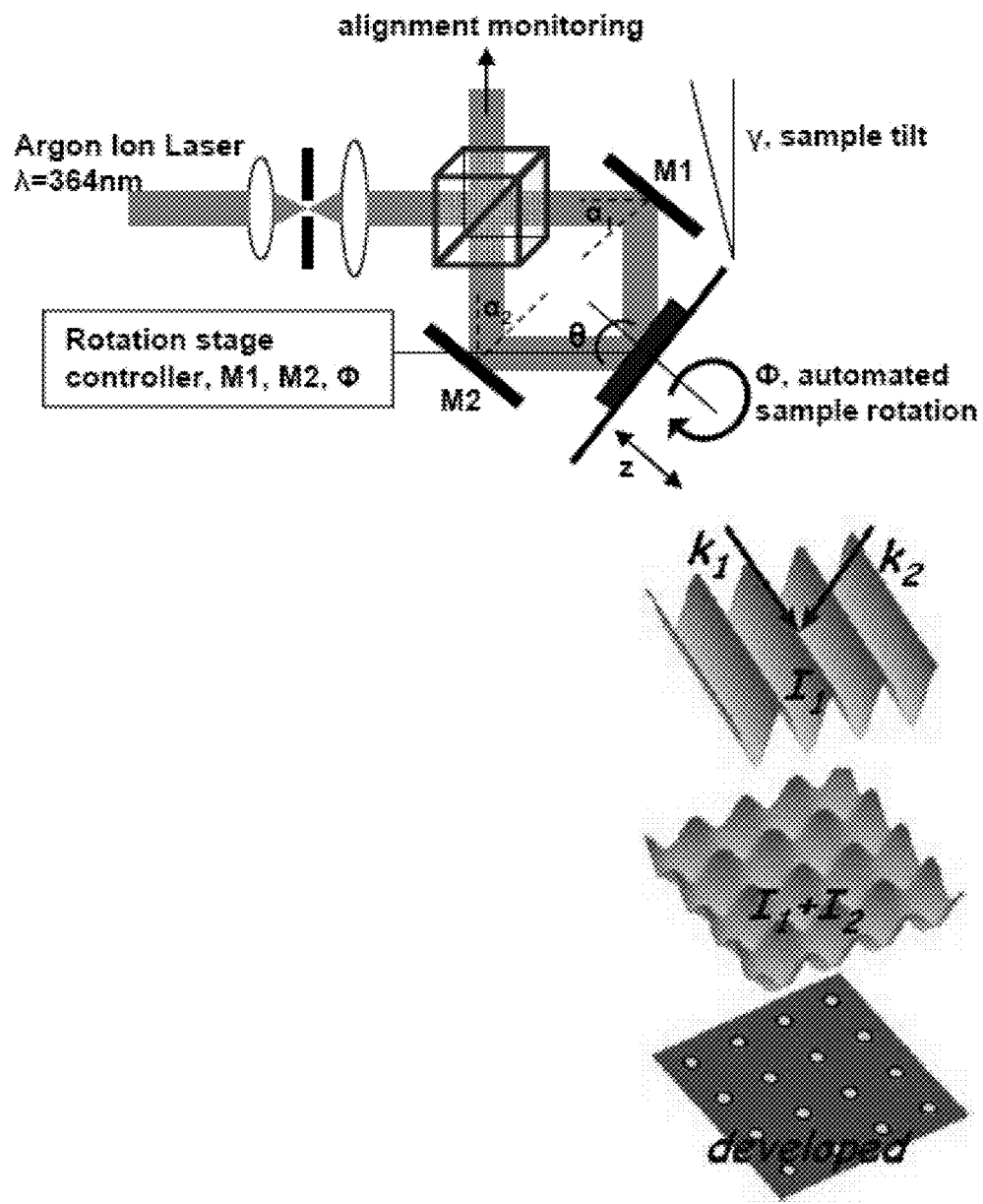
FIG. 6 shows in more detail one of the fabrication steps of FIG. 5.

FIG. 9) were fabricated using holographic lithography where two interfering UV laser beams were incident upon negative MicroChem SU8 photoresist placed on top of a 1.2 mm thick SiO$_2$ substrate. In order to achieve a hole pattern, each sample was exposed and then rotated 90° for an additional exposure step. Prior to the exposure, the SiO$_2$ substrate was cleaned in a Pirahna bath (1:1:5 of H$_2$O:H$_2$O$_2$:H$_2$SO$_4$) solution for 30 minutes and the surface was dehydrated by baking on a hot plate at 200° C. for 5 minutes. A 2 μm layer of SU8-5 was spin deposited at 3000 rpm. The samples were exposed (as shown in FIG. 6) with a Coherent Innova 300 Argon-Ion laser centered at 364 nm with a 150 mJ dosage per exposure, and followed by a convection oven soft bake for 1 minute.

Figure 7:
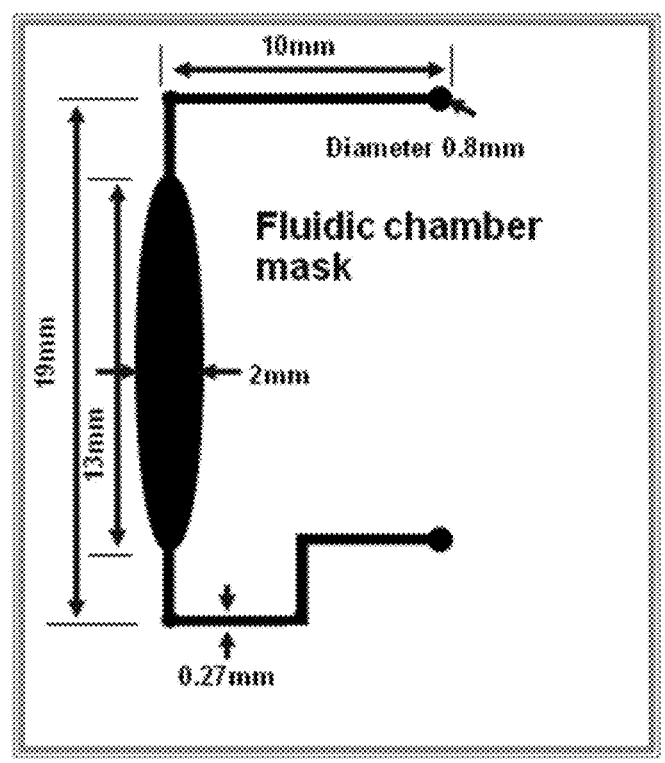
FIG. 7 shows a fluidic chamber mask.

The SU8 development time was 3 minutes and it was followed by an IPA rinse. A 5 nm thick Titanium adhesion layer, followed by a 100 nm gold layer was sputtered onto the samples using the Denton Discovery 18 Sputter System. Fluidic chambers made of Polydimethylsiloxane (PDMS) were affixed on top of each sample's grating array using oxygen plasma. It should be noted that PDMS does not readily bond to Au, hence a region of bare SiO$_2$ was left on each sample, surrounding the 4 cm$^2$ gold grating array, in order to facilitate in the PDMS adhesion. The main portion of the fluidic chamber was 13 mm by 2 mm in size, allowing for both beams to be easily directed onto the grating portion of the sample. The fluidic chamber mask is shown in FIG. 7, with the main portion of the chamber having dimensions of 13 mm by 2 mm in size, as shown.

The grating array sample shown in FIG. 5a has a 1400 nm period with 600 cm hole diameter and 1 cm$^2$ area. The hole size is significant for FWHM of the DTF.

Figure 8:
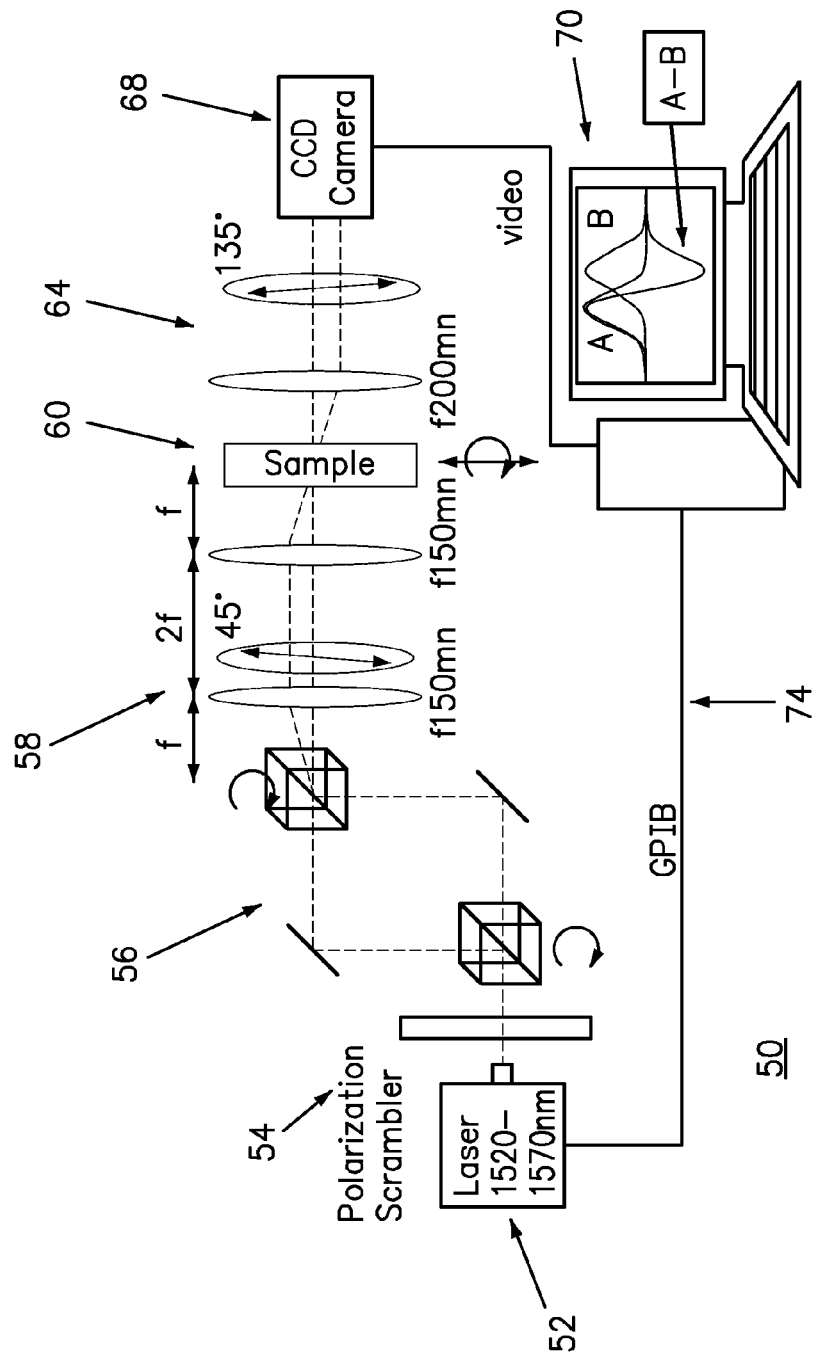
FIG. 8 shows a block diagram of an experimental setup.

FIG. 8 shows an experimental setup 50 used to measure SPR response to different concentration ethylene glycol solutions. The setup shown in FIG. 8 consists of a tunable New Focus laser 52 in a range of 1520 nm-1570 nm connected to a polarization scrambler 54 in order to randomize the polarization state of input light and to minimize polarization dependent loss associated with the components of the experimental setup. In order to perform the differential measurement, the collimated beams incident at different angles need to meet at the same spot on the sample 60 shown in FIG. 8.

This is accomplished by using two polarization independent beam splitters positioned in a Mach-Zehnder configuration 56, where two beams separated by the first splitter are multiplexed at the same spot onto the second splitter; then both beams from the second splitter are imaged with a 4-F telecentric imaging system 58 on to the sample surface 60, where the relative angle between the two beams can be fine adjusted by rotation of the second beam splitter. Equal beam path lengths ensured spots from the two beams to be equal sized. Light emerging from the sample 60 is then spatially Fourier transformed by a lens 64 into two parallel beams, where each one is receipted by a photodetector for the differential measurement.

In lieu of a pair of detectors, we used an Indigo Merlin CCD camera 68 to record light from the two beams and thus obtain the DTFs corresponding to the two angles of incidence at the sample. The differential signal was then calculated by the computer 70. A pair of polarizers was placed with one element in front and one element behind the sample, where their polarization state was set to a cross position, to suppress directly transmitted light (nonresonant transmission) and isolate the observation of SPP resonance. The sample along with the microfluidic delivery system was mounted on a rotational stage.

Prior to measurement, the laser wavelength was set to 1545 nm and the sample was rotated to obtain equal power in the two detectors. In this way, $\lambda$=1545 nm was positioned midway between the maxima of the two DTFs at the zero-crossing of the differential signal (see FIG. 1c and FIG. 4c).

The detector output was then monitored while fluids of varying refractive indices were introduced into the fluidic channel. Before a measurement was performed, methanol was advanced into the PDMS chamber in order to clean the sample. H$_2$O was used to flush the methanol and various concentrations of an ethylene glycol solution, ranging from 1.9% to 9.1%, were introduced into the chamber. The measurement process was automated via a Labview program with a GPIB interface 74 to the New Focus tunable laser 52 and video grabbing card to the CCD 68.

Figure 9A:
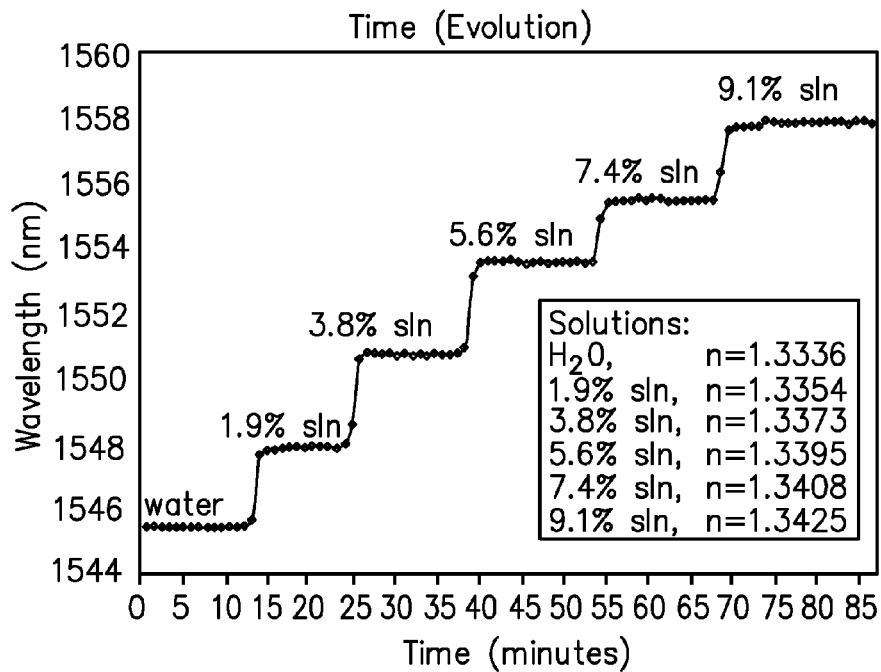
FIG. 9a shows a time evolution of wavelength relative to time.

FIG. 9 reports the results of an experiment in which six different ethylene glycol/water solutions (abbreviated "sln") were sequentially introduced into the fluidic chamber. The refractive indices of the solutions, measured separately with a refractometer, are indicated in the inset in FIG. 9a.

Throughout the test, the laser wavelength was continuously adjusted to track the zero-crossing of the differential signal by maintaining equal power in the two detectors. The zero-crossing wavelength is plotted in FIG. 9a as a function of time, and in FIG. 9b as a function of the refractive index of the fluid.

Figure 9B:
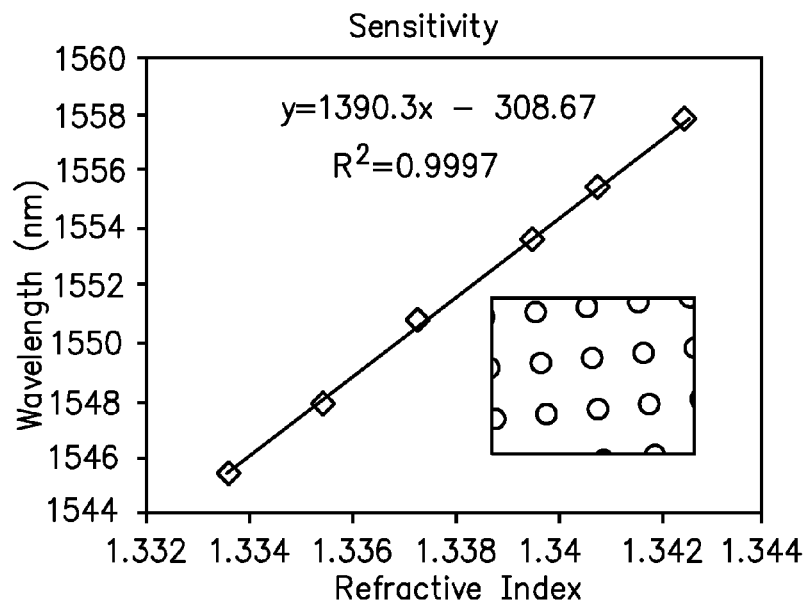
FIG. 9b shows sensitivity of wavelength relative to refractive index.

From the linear curve fit in FIG. 9b the sensitivity figure $S_\lambda \equiv d\lambda/dn$=1390 nm/RIU. This is consistent with the analytical expression given by Pang et al. for plasmonic mode (1,0) and grating period close to 1400 nm.

The evolution of the SPP differential detection spectral response is shown in FIG. 9 as a function of time, in which FIG. 9(a) shows different concentrations of ethylene glycol are introduced at various time intervals, and FIG. 9(b) shows a linear fit of the time evolution measurement, where the sensitivity (response to index variation) is represented by the slope. In this case the sensitivity is 1390 nm/RIU, and the grating period is 1400 nm. The y-axis in FIG. 9b represents A-B zero crossing in wavelength and the x-axis represents the refractive index.

We have presented a differential measurement technique for a nanoplasmonic sensor operating in the transmission regime. The differential technique provides a two fold increase in the dynamic range of intensity due to the contribution of the second DTF, it decreases the measurement time due to the tracking of just the zero crossing point, in addition to extending the dynamic range and signal to noise ratio. The differential DTF intensity measurement can be amplified by controlling the resonance FWHM, where a narrower FWHM translates into a steeper differential slope. We bypassed the cumbersome Center of Mass (CoM) and only used smoothing for our experiment, where we achieved detection resolution on the order of $10^{-5}$ RIU. The sensitivity can be improved by increasing the fill factor of the nanohole array at the expense of a reduction in the signal level.

From the above description of the surface plasmon resonance sensor and method, it is apparent that various techniques may be used for implementing the concepts of the present invention without departing from its scope.

Figure 10:
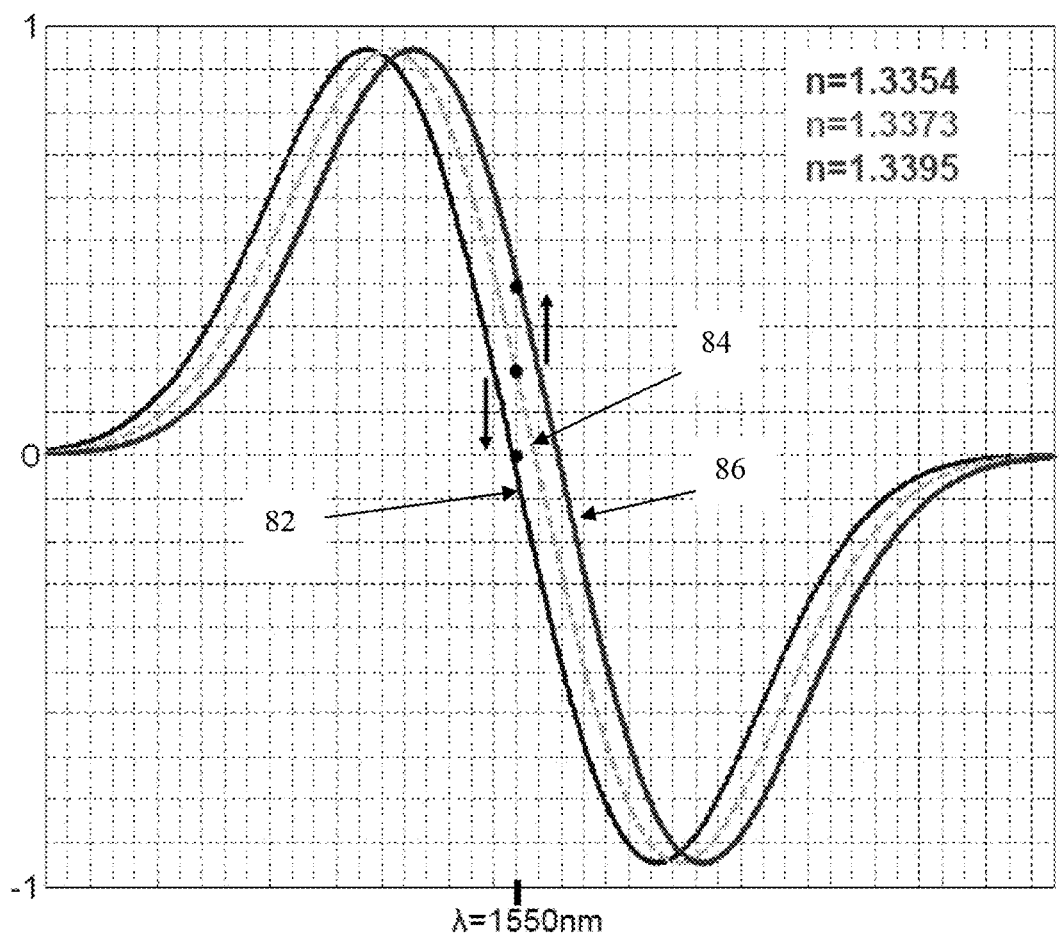
FIG. 10 shows a differently method of the present invention for intensity detection.

For example, we can also use our differential method for intensity detection. In this scenario as shown in FIG. 10, after we calibrate the system, we position ourselves at a single wavelength corresponding to the zero crossing of our calibration differential (middle curve 84 as shown in FIG. 10 and corresponding to an index of n=1.3373). Then as the solution/gas formulation is replaced by a different one (and thus the corresponding refractive index changes as shown by left curve 82, with an index of n=1.3354, or right curve 86 with n=1.3395 in FIG. 10), we just monitor the change in intensity. With our differential detection method the range of measureable intensity is doubled.

For the differential intensity detection, the slope of the differential curve determines the sensitivity. A very steep slope directly translates into higher sensitivity.

Also, the differential detection method can also be set up and used in reflection mode, where the closed-loop configuration shown in FIG. 4a includes a laser means for imaging a pair of laser beams onto a nanohole array to excite surface plasmon resonance and form a pair of reflected laser beam emerging from the nanohole array. The laser means then forms a pair of reflected parallel laser beams emerging from the nanohole array which impinge on a pair of detectors.

In one preferred embodiment, a surface plasmon resonance sensor is described, having a metal-dielectric interface formed by microfluidic channels integrated with metal-dielectric layer chips. One preferred method includes the steps of imaging a pair of collimated laser beams at different angles of incidence onto substantially the same spot on a metal nanohole array sample at the metal-dielectric interface to excite surface plasmons on the array sample and forming a pair of transmitted laser beams emerging from the array sample; forming a pair of parallel laser beams corresponding to the pair of transmitted laser beams; obtaining a pair of device transfer function (DTF) signals from the pair of parallel laser beams, where each respective DTF signal has a different angle of incidence and an intensity peak at a different wavelength relative to a reference wavelength; and calculating a difference signal from the pair of DTF signals, where the difference signal has positive and negative values about a zero crossing axis which are representative of transmittivity relative to wavelength and where a resulting shift in the location of the difference signal at the zero crossing axis represents a changing refractive index of the dielectric at the metal-dielectric interface.

The described embodiments are to be considered in all respects as illustrative and not restrictive. It should also be understood that the surface plasmon resonance sensor and corresponding method is not limited to the particular embodiments described herein, but is capable of many embodiments without departing from the scope of the claims.

What is claimed is:

1. In a surface plasmon resonance sensor having a metal-dielectric interface formed by microfluidic channels integrated with metal-dielectric layer chips, the method comprising:
    imaging a pair of collimated laser beams at different angles of incidence onto substantially the same spot on a metal nanohole array sample at the metal-dielectric interface to excite surface plasmons on the array sample and forming a pair of transmitted laser beams emerging from the array sample;
    forming a pair of parallel laser beams corresponding to the pair of transmitted laser beams;
    obtaining a pair of device transfer function (DTF) signals from the pair of parallel laser beams, where each respective DTF signal has a different angle of incidence and an intensity peak at a different wavelength relative to a reference wavelength;
    calculating a difference signal from the pair of DTF signals, where the difference signal has positive and negative values about a zero crossing axis which are representative of transmittivity relative to wavelength and where a resulting shift in the location of the difference signal at the zero crossing axis represents a changing refractive index of the dielectric at the metal-dielectric interface.

2. The method of claim 1 where the resonance sensor is in a closed loop configuration.

3. The method of claim 2 including obtaining the DTF signals at FWHM (Full Width Half Maximum) values.

4. The method of claim 3 where the array sample is a grating array.

5. A surface plasmon resonance sensor having a metal-dielectric interface formed by microfluidic channels integrated with metal-dielectric layer chips, the sensor comprising:
    laser means for generating and imaging a pair of collimated laser beams at different angles of incidence onto substantially the same spot on a metal nanohole array sample at the metal-dielectric interface to excite surface plasmons on the array sample and forming a pair of transmitted parallel laser beams emerging from the array sample;
    processor means for obtaining a pair of device transfer function (DTF) signals from the pair of parallel laser beams, where each respective DTF signal has a different angle of incidence and an intensity peak at a different wavelength relative to a reference wavelength and for calculating a difference signal from the pair of DTF signals, where the difference signal has positive and negative values about a zero crossing axis which are representative of transmittivity relative to wavelength and where a resulting shift in the location of the difference signal at the zero crossing axis represents a changing refractive index of the dielectric at the metal-dielectric interface.

6. The sensor of claim 5 wherein the sensor operates in a closed loop configuration.

7. The sensor of claim 6 wherein the processor means obtains the DTF signals at FWHM (Full Width Half Maximum) values.

8. The sensor of claim 7 where the array sample is a grating array.

9. The sensor as in claim 8 where the laser means includes a laser for generating a range of tunable laser beams and beam splitter means for generating the pair of collimated laser beams.

10. The sensor as in claim 9 including detector means for obtaining the DTF signals.

11. The sensor as in claim 10 including a computer for calculating the difference signal.

12. A surface plasmon resonance sensor operating in a closed loop configuration and having a metal-dielectric interface formed by microfluidic channels integrated with metal-dielectric layer chips, the sensor comprising:

laser means for generating and imaging a pair of collimated laser beams at different angles of incidence onto substantially the same spot on a metal nanohole grating array sample at the metal-dielectric interface to excite surface plasmons on the array sample and forming a pair of parallel laser beams emerging from the array sample;

processor means for obtaining a pair of device transfer function (DTF) signals at FWHM (Full Width Half Maximum) values from the pair of parallel laser beams, where each respective DTF signal has a different angle of incidence and an intensity peak at a different wavelength relative to a reference wavelength and for calculating a difference signal from the pair of DTF signals, where the difference signal has positive and negative values about a zero crossing axis which are representative of transmittivity relative to wavelength and where a resulting shift in the location of the difference signal at the zero crossing axis represents a changing refractive index of the dielectric at the metal-dielectric interface.

13. The sensor of claim 12 where the processor means includes a pair of detectors and where the pair of parallel laser beams impinge on the pair of detectors.

14. The sensor of claim 12 where the pair of collimated laser beams are transmitted through the grating array sample.

15. The sensor of claim 12 where the pair of collimated laser beams are reflected from the grating array sample.

16. The sensor of claim 12 including means for detecting the differential intensity of the pair of parallel laser beams.

* * * * *